United States Patent [19]

Ogawa et al.

[11] Patent Number: 5,528,644
[45] Date of Patent: Jun. 18, 1996

[54] X-RAY CT SCANNER AND METHOD OF COLLECTING IMAGE DATA IN THE SAME

[75] Inventors: Yukihiro Ogawa, Otawara; Yusuke Toki, Utsunomiya, both of Japan

[73] Assignee: Kabushiki Kaish Toshiba, Kawasaki, Japan

[21] Appl. No.: 377,351

[22] Filed: Jan. 24, 1995

[30] Foreign Application Priority Data

Jan. 24, 1994 [JP] Japan .................................. 6-005747

[51] Int. Cl.$^6$ ...................................................... A61B 6/03
[52] U.S. Cl. .......................... 378/8; 378/901; 364/413.19
[58] Field of Search ......................... 364/413.16, 413.19; 378/4, 8, 901

[56] References Cited

U.S. PATENT DOCUMENTS

5,043,890  8/1991  King .................................. 364/413.21
5,457,724  10/1995  Toth .................................. 378/4

*Primary Examiner*—David P. Porta
*Assistant Examiner*—David Vernon Bruce
*Attorney, Agent, or Firm*—Oblon, Spivak, McClelland, Maier & Neustadt

[57] ABSTRACT

In an X-ray CT scanner, a first field of view corresponding to a reconstructed area of an image to be displayed is set. An original image data are reconstructed on the basis of a plurality of projection data in a patient in response to the first field of view. Whether or not an imaged region in the patient is larger than the first field of view is judged according to referring the original image data. A second field of view including the imaged region wholly is set in case that the imaged region is larger in area than the first field of view. Beam hardening correction data are produced on the basis of the projection data in the second field of view. The projection data are processed into the image corresponding to the first field of view with an aid of the correction data.

9 Claims, 5 Drawing Sheets

FIG. 7A PRIOR ART — ENERGY SPECTRUM OF INCIDENT X-RAY

FIG. 7B PRIOR ART — ABSORPTION SPECTRUM

FIG. 7C PRIOR ART — ENERGY SPECTRUM OF TRANSMITTED X-RAY

FIG. 8 PRIOR ART

X-RAY CT SCANNER AND METHOD OF COLLECTING IMAGE DATA IN THE SAME

BACKGROUND OF THE INVENTION

1. Field of the Invention

The present invention relates to an X-ray computed tomography (CT) scanner and a method of collecting image data in the X-ray CT scanner.

More particularly, the present invention relates to an X-ray CT scanner providing means for performing beam hardening correction and to a method of collecting image data in the X-ray CT scanner.

2. Description of the Prior Art

An X-ray CT scanner detects X-rays transmitting through an object being examined and computes absorption coefficients of the X-rays inside the object such as a human body. In accordance with the absorption coefficients, the X-ray CT scanner can reconstruct image data of the sliced planes inside the object.

Figure 7A:
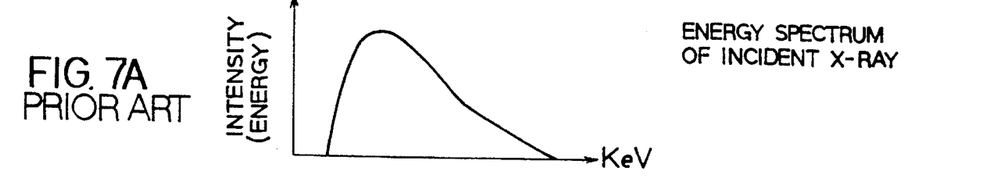
FIG. 7A is a graph illustrating an energy spectrum of an incident X-ray according to the conventional example.
Figure 7B:
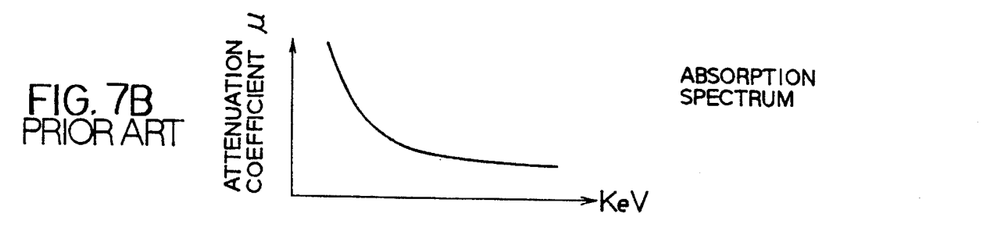
FIG. 7B is a graph illustrating an absorption spectrum inside a human body according to the conventional example.
Figure 7C:
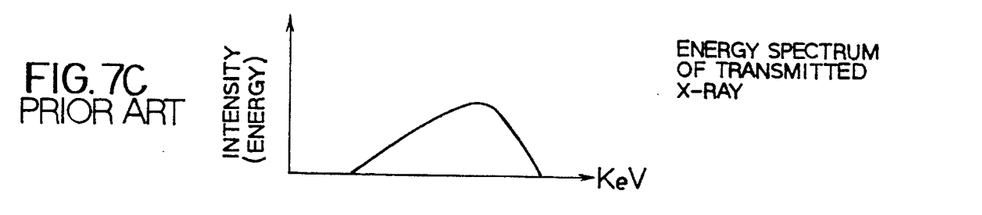
FIG. 7C is a graph illustrating an energy spectrum of a permeated X-ray according to the conventional example.

An X-ray source used for the X-ray CT scanner is the polychromatic source which has multispectrum. That is, the X-ray has a certain energy width on an energy spectrum. For example, FIG. 7A shows the energy spectrum of an incident X-ray into a human body. Moreover, FIG. 7B shows an absorption spectrum inside the human body. The symbol $\mu$ in FIG. 7B stands for an attenuation coefficient. According to the FIG. 7B, when the X-ray passes through the human body, the X-ray which has low energy level (soft X-ray) is more attenuated than the X-ray which has high energy level (hard X-ray). Therefore, as shown in FIG. 7C, the energy spectrum of the transmitted X-ray detected with an X-ray detector has constituted that the high level energy part increases relatively. As a result, the permeated X-ray has hardened (hereinafter this X-ray hardening phenomenon is called beam hardening).

This beam hardening is more remarkable as the permeation length of the X-ray in the human body is longer. Hereinafter, the length is called the X-ray path length. According to the beam hardening, the CT-value in the reconstructed image decreases from the area corresponding to its circumference of the human body to the center area. Consequently, artifacts appear in the reconstructed image.

In order to solve the problem of the artifacts appearance, the beam hardening correction (hereinafter called BHC), as the correction process with the quality of X-ray, has performed. For example, there is the second pass BHC in the BHC.

In the second pass BHC, the process will be described as follows. That is, the area to be reconstructed is set in advance (hereinafter called the field of view; FOV), the FOV including an region to be imaged, such as a sliced plane in the human body (hereinafter the region is called imaged region). The original image data are reconstructed on the basis of the plurality of projection data In the FOV. Next, a plurality of X-ray path length of the bone part and the mineral part, such as water part, in the reconstructed image are computed. A plurality of beam hardening correction data are generated by using the plurality of X-ray path length of the bone part and the mineral part. Then, image data are reconstructed by using the beam hardening correction data and the original image data.

Figure 8:
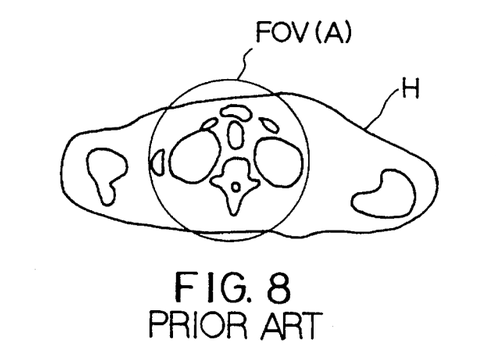
FIG. 8 is a diagram illustrating a state that the imaged region is larger than the first field of view.

However, the foregoing process of the second BHC, for example, a magnification display of an interest area in the imaged region or zooming display (display of zooming in the interest area in the imaged region) and so on, in case that the imaged region H is larger than the FOV (A) as shown in FIG. 8, the X-ray path length in the direction of the large part is not computed correctly. As a result, it is difficult to perform the second BHC process correctly. Therefore, the artifacts also appear the border between the bone part and the mineral part in the reconstructed image. The artifacts cause a deterioration in the quality of the reconstructed image.

SUMMARY OF THE INVENTION

The present invention is directed to overcome the foregoing problems. Accordingly, it is an object of the present invention is to provide an X-ray CT scanner and a method of collecting image data in the same capable of performing the BHC process in case that the imaged region is larger than the FOV.

It is another object of the present invention to provide an X-ray CT scanner and a method of collecting image data in the same capable of reducing the artifacts of the reconstructed image and improving the quality of the reconstructed image.

In order to achieve such objects, according to one aspect of the present invention, there is provided an X-ray CT scanner, in which an image is produced on the basis of a plurality of projection data of an object being examined and the image are displayed, the scanner comprising means for setting a first field of view corresponding to a reconstructed area of the image, means for reconstructing original image data on the basis of the projection data in response to the first field of view, means for judging whether or not an imaged region in the object is larger than the first field of view means for setting a second field of view including the imaged region wholly in case that the imaged region is larger than the first field of view, means for producing beam hardening correction data on the basis of the projection data in the second field of view, and means for processing the projection data into the image corresponding to the first field of view with an aid of the correction data.

In preferred embodiments of this aspect, the judgement is performed automatically.

This aspect of the present invention has an arrangement that the Judgement means is comprised of an element for detecting each CT-value of a plurality of pixels located in a circumference of the original image data and an element for judging whether or not the each CT-value is CT-value of air.

This aspect of the present invention has an arrangement that the beam hardening correction data are composed of correction components of the projection data.

This aspect of the present invention has an arrangement that the projection data processing means comprises means for reconstructing correction image data composed of correction components of the original image data by using the correction data according to the first field of view and means for producing the image by synthesizing the correction image data and the original image data.

In order to achieve such objects, according to another aspect of the present invention, there is provided a method of collecting image data in an X-ray CT scanner, in which an image is produced on the basis of a plurality of projection data of an object being examined and the image is displayed, the method comprising setting a first field of view corresponding to a reconstructed area of the image, reconstructing original image data on the basis of the projection data in response to the first field of view, judging whether or not an imaged region in the object is larger than the first field of view setting a second field of view including the imaged region wholly in case that the imaged region is larger than the first field of view, producing beam hardening correction data on the basis of the projection data in the second field of view, and processing the projection data into the image corresponding to the first field of view with an aid of the correction data.

In an X-ray CT scanner, a first field of view corresponding to a reconstructed area is set by the setting means. Original image data are reconstructed by the reconstructing means on the basis of a plurality of projection data in an object to be examined in response to the first field of view.

Now, it is assumed that the first field of view is not larger than an imaged region in the object is set. At that time, each CT-value of a plurality of pixel located in a circumference of the original image data is detected by the detecting element and it is Judged that the imaged region is larger than the first field of view according to finding out whether or not the each CT-value is CT-value of air by the judging element. Then, a second field of view including the imaged region wholly is set by the second field of view setting means. Beam hardening correction data are produced by the producing means on the basis of the projection data in the second field of view. The projection data are processed into the image by the processing means corresponding to the first field of view with an aid of the correction data.

According to the present invention, as it is possible to perform the BHC process easily in case that the imaged region is larger than the FOV, most of the artifacts which appear in the reconstructed image may be reduced and the accuracy of the CT-value in the reconstructed image data may be improved. Therefore, the clearness of the image is still more improved. Moreover, as it is possible to Judge whether or not the imaged region is larger than the FOV automatically, for example as detecting each CT-value of the plurality of pixel which are located in the circumference of the image data, the Judgement may perform rapidly.

BRIEF DESCRIPTION OF THE DRAWINGS

Other objects and aspects of the invention will become apparent from the following description of an embodiment with reference to the accompanying drawings in which.

DESCRIPTION OF THE PREFERRED EMBODIMENTS

A preferred embodiment of the present invention will now be described with reference to the drawings.

Figure 1:
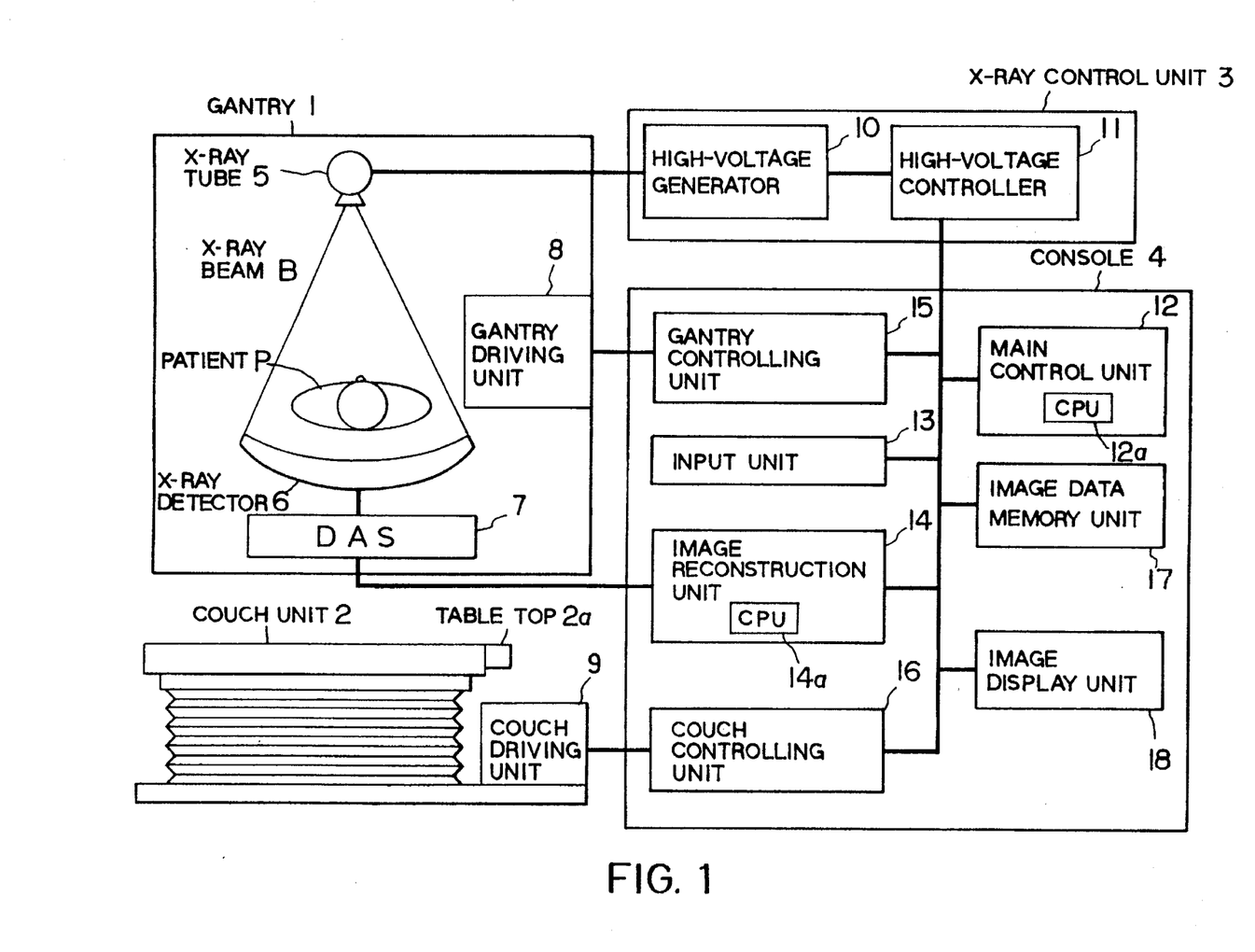
FIG. 1 is a schematic structural view of an X-ray CT scanner according to the present invention.

FIG. 1 is an overall block diagram of an X-ray CT scanner according to this embodiment.

The X-ray CT scanner shown in FIG. 1, for example, is a rotate/rotate type CT scanner. The X-ray CT scanner is provided with a gantry 1 having an X-ray tube 5 and an X-ray detector 6 and a couch unit 2 having a tabletop 2a on which a patient P lies as an object being examined. The X-ray CT scanner is also provided with an X-ray control unit 3 for controlling the X-ray beam radiated by the X-ray tube 5 and a console 4 to control the whole X-ray CT scanner.

The gantry 1 has the X-ray tube 5 and the X-ray detector 6 which is placed opposite to the X-ray tube 5. The X-ray tube 5 irradiates X-rays (X-ray beams B) toward the patient P. The X-ray detector 6 has a plurality of channels for detecting the X-ray beams B, which are transmitted through the patient P. The X-ray detector 6 is constructed so as to convert the X-ray beams B into the quantity of electric charge (the quantity of electric charge is called X-ray data hereinafter). The gantry 1 also has a data acquisition system (DAS) 7 for collecting a plurality of projection data by receiving the X-ray data fed from the X-ray detector 6 and a gantry driving unit 8 to rotate the X-ray tube 5 and the X-ray detector 6 in a body with scanning.

The couch unit 2 is provided with a couch driving unit 9 to move the tabletop 2a along to the direction of the patient's body axis and to move vertically the couch unit 2. The couch driving unit 9 is constructed so as to carry the patient P into the fixed position in the gantry 1 and to carry the patient P which is inside the gantry 1 to the fixed position on the couch unit 2 by moving the tabletop 2a along the direction of the patient's body axis.

The X-ray controller 3 is provided with a high-voltage generator 10 and a high-voltage controller 11. The input side of the high-voltage generator 10 is connected with a high-voltage controller 11. The high-voltage generator 10 is constructed so as to supply high voltage to the X-ray tube 5 in response to the control signals outputted from the high-voltage controller 11.

The console 4 is provided with a main control unit 12 for controlling the whole X-ray CT scanner. This main control unit 12 has a central processing unit (CPU) 12a and memory (not shown). In the memory, the procedure of the process which the CPU 12a performs and the data needed for the process are memorized previously.

The console 4 is provided with an input unit 13 which has a console panel or other similar inputting device. The input unit 13 is able to set various scanning conditions and display conditions, for example, an FOV, magnification display, zooming display, and so on, according to operating the console panel by an operator. Moreover, the operator is able to set the FOV according to a size of an imaged region in the patient P.

The console 4 also has an image reconstruction unit 14. The image reconstruction unit 14 is provided with a local CPU 14a (hereinafter called the second CPU) performing the process shown in FIGS. 2 and 3 in response to the control signals outputted from the CPU 12a. The image reconstruction unit 14 is also provided with a memory (not shown) for storing the processing result of the second CPU 14a. Moreover, to calibrate the sensitivity of the X-ray detector 6, the memory stores data composed of the known CT-value for a fluctuation correction as reference substance, which are CT-values of the water phantom (hereinafter the data are called water phantom data.

The image reconstruction unit 14 performs the image reconstruction process, for example, by using back projection method, and the second pass BHC process by receiving the projection data fed from the DAS 7, the projection data being included in the FOV set by the input unit 13.

The console 4 is provided with a gantry controlling unit 15 for controlling the gantry driving unit 8 so as to control the driving condition (driving quantities, driving speed, etc) of the gantry 1, a couch controlling unit 16 for controlling the couch driving unit 9 so as to control the driving condition (driving quantities, driving speed, etc) of the couch 2a and tabletop 2a, an image data memory unit 17 for memorizing the image data reconstructed by the image reconstruction unit 14, a image display unit 18 for displaying the image data reconstructed by the image reconstruction unit 14 directly or the image data memorized by the image data memory unit 17. The image display unit 18 is constructed so as to be able to perform the magnification display, the zooming display, and so on in response to the control signals outputted from the CPU 12a.

Further, the high-voltage controller 11, the image reconstruction unit 14, the gantry controlling unit 15, the couch controlling unit 16, the image data memory unit 17, and the image display unit 18 are connected via a bus with each other.

Next, according to FIG. 2, the image reconstruction process performed by the second CPU 14a will be explained.

When the second CPU 14a is supplied with the image reconstruction signals from the CPU 12a, the second CPU 14a reads the plurality of projection data fed from the DAS 7 and stores the memory with the plurality of projection data (step S1). Next, the second CPU 14a performs the preprocess with the plurality of projection data included in the FOV by using the water phantom data. The preprocess includes the correction process of the fluctuation in sensitivity of the detector 6, the normalization process, and so on (step S2). By using this projection data performed the preprocess, the CPU 14a performs convolution process (step S3). Next, the CPU 14a performs back projection process so as to generate reconstructed image data as original image data (step S4).

Figure 2:
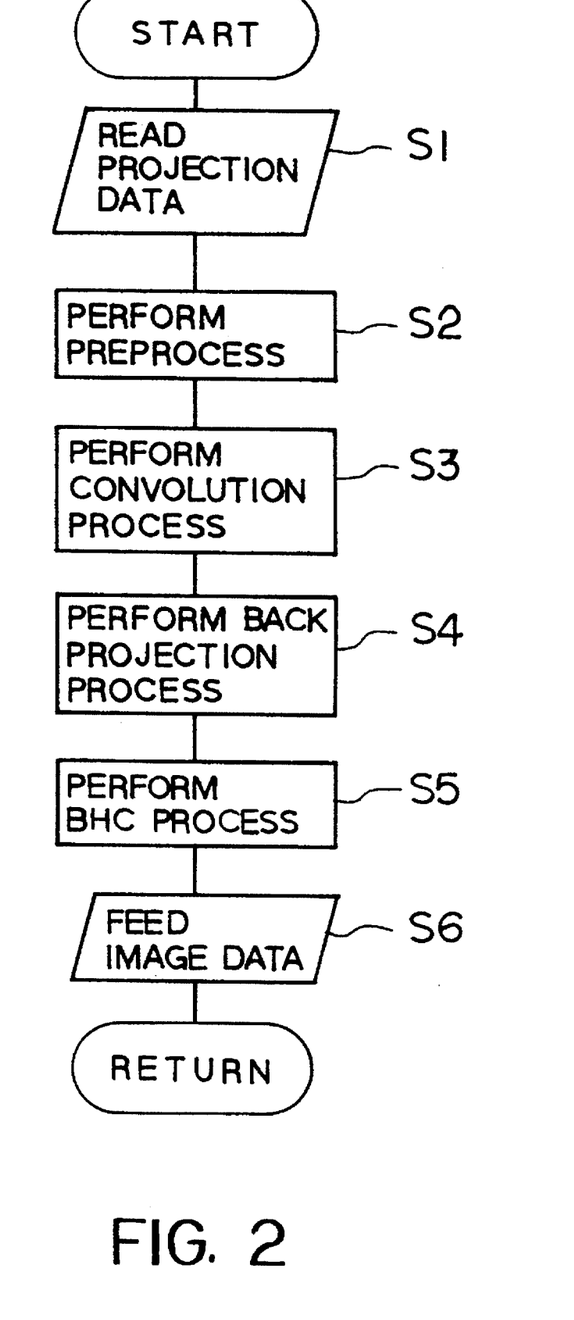
FIG. 2 is a schematic flow chart showing an example of a process performed by a second central processing unit according to the present invention.
Figure 3:
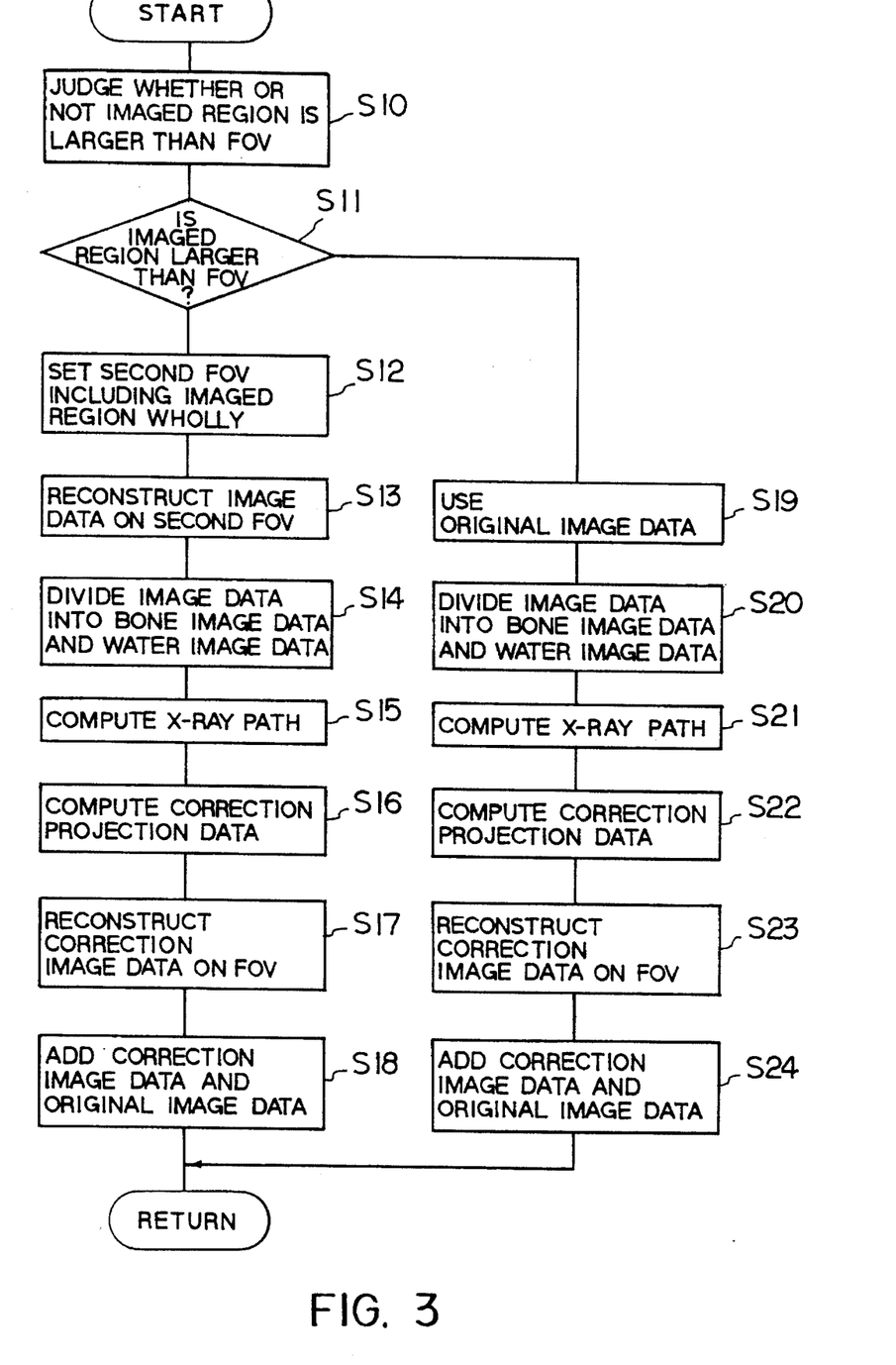
FIG. 3 is a schematic flow chart showing the process of the second central processing unit corresponding to step S5 in FIG. 2 in detail.

Then, the second CPU 14a performs the BHC process, as shown in FIG. 3, with the reconstructed image data so as to generate image data which is given to the BHC process (step S5). The second CPU 14a feeds this image data into the image data memory unit 17 or the image display unit 18 (step S6). After that, the process returns to main process.

Moreover, according to FIG. 3, the process of the second CPU 14a on step S5 will then be explained.

The second CPU 14a judges whether or not the imaged region is larger in area than the FOV. In one method of the judgements, the second CPU 14a detects each CT-value of the plurality of the pixels, which are located in the circumference of the original image data reconstructed on the FOV (step S10). The second CPU 14a Judges that the imaged region is larger than the FOV (judges YES) in case that all the detected CT-values of the plurality of pixels are not the CT-value of the air (generally −1000) or judges that the imaged region is not larger than the FOV (judges NO) in case that all the detected CT-values are the CT-value of the air (step S11).

When the Judgement at step S11 is YES, the second CPU 14a sets a second FOV including the imaged region wholly (step S12). Next, the second CPU 14a reconstructs the image data on the basis of the projection data which are included in the second FOV (step S13), the process of the second CPU 14a goes on to step S14. In addition, the water phantom data used at step S13 are the same as the water phantom data used with the FOV of the original image data.

The second CPU 14a divides the image data generated at step S13 into bone image data and water image data (step S14). Then, the second CPU 14a computes the X-ray path length of the bone image data and the water image data, respectively. Moreover, at the pixels out of the FOV, the CT-value of the air is the reference value (calibration on the air) because of using the same water phantom data with the original image data. Therefore, the second CPU 14a adds the CT-value of −1000 to the pixels out of the FOV and, after that, computes the X-ray path length (step S15).

Then, the second CPU 14a computes the beam hardening quantity of the bone image data and the water image data respectively by using the x-ray path length and computes the correction projection data which are composed of correction components of the projection data on the basis of the beam hardening quantity (step S16).

Next, the second CPU 14a reconstructs the correction image data which are composed of correction components of the original image data by using the correction projection data on the FOV (step S17).

Still further, the second CPU 14a adds the correction image data and the original image data so as to produce the image data performed the beam hardening correction (step S18), the process goes on to step S6.

On the other hand, when the judgement at step S11 is NO, the second CPU 14a uses the original image data (step S19) and performs the process from step S20 to step S24 which are the same as step S14 to step S18, the process goes on to step S6.

The operation of this embodiment will now be described.

First, the operator puts the patient P on the tabletop 2a of the couch unit 2. At this time, the operator operates the couch controlling unit 16 so as to supply the couch driving unit 9 with the control signals. The couch driving unit 9 receives the control signals and drives so that the tabletop 2a rises and moves horizontally towards the gantry 1. As a result of the movement of the tabletop 2a, the patient P is carried into a fixed position in the gantry 1.

Next, the operator operates the console panel with the input unit 13 so as to set scan conditions, for example the number of scans, sliced positions (the positions of the sliced (scanned) planes in the patient P, such as a position of a first scanned plane and position of a end scanned plane), and so on. The set of the scanned planes compose an examined field in the patient P. Moreover, the operator operates the console panel so as to set the imaged sliced plane which is of desirable sliced position to be imaged (hereinafter the imaged sliced plane is called imaged region).

Still further, the operator also operates the console panel so as to set a display condition, for example, the FOV, and so on. The FOV set at first is of a regular size which includes the imaged region.

Then, the operator operates the console panel so as to output the scan performing order to the CPU 12a and the second CPU 14a.

In response to the scan performing order, the CPU 12a reads out the data which include the X-ray radiation voltage, the gantry rotation quantity, sliced positions, and so on, according to the scan conditions and the display conditions, from the memory. Next, the CPU 12a supplies the control signals which are based on the data to the high-voltage controller 11, the image reconstructing unit 14, the gantry controlling unit 15, and the couch controlling unit 16.

The couch controlling unit 16 drives the couch driving unit 9 by receiving the control signals. The couch driving unit 9 makes the tabletop 2a move along the direction of the patient's body axis into the gantry 1 so as to adjust the position of the patient P to the first sliced position set by the scan condition.

The high-voltage controller 11 controls the voltage generated by the high-voltage generator 10, which is supplied to the X-ray tube 5, in response to the control signals. As a result, the X-ray beam B is radiated toward the patient P. In synchronization with the scanning start, the gantry controlling unit 15 drives the gantry driving unit 8 in response to the control signals so as to rotate the gantry 1 by a required angle. As a result, the plurality of X-ray data from every direction about the first sliced plane in the examined area are detected by the X-ray detector 6.

While the scanning is repeated, the couch controlling unit 16 drives the couch driving unit 9 in response to the control signals so as to slide the tabletop 2a until the end of the sliced position at every required sliced width. Consequently, the plurality of X-ray data from every sliced planes in the examined field are detected by the X-ray detector 6. The plurality of X-ray data is sent to the DAS 7 and the plurality of projection data are collected by the DAS 7.

Next, the projection data corresponding to the imaged region are sent to the image reconstruction unit 14. As the second CPU 14a performs the process shown in FIG. 2, the CPU 14a reads in the projection data and performs the preprocess, the convolution process, and back projection process with the projection data (refer to steps S1 to S4 in FIG. 2). As a result, the reconstructed image data (original image data) is generated.

After that, the second CPU 14a performs the BHC process on step S5. That is, the second CPU 14a performs the process with the original image data at steps S10, S11, and steps S19 to S24.

Namely, the second CPU 14a detects each CT-value of the plurality of pixels which are located in the circumference of the image data in order to judge whether or not the imaged region is larger in area than the original image data corresponding to the FOV (refer to step S10 in FIG. 3). Now, as the FOV set at first is of the regular size which includes the imaged region, all the detected CT-values become the CT-value of the air (generally −1000). Therefore, it is judged that the imaged region is not larger than the FOV (the judge is No) (refer to step S11 in FIG. 3).

According to the judgement at step S11, the original image data is used by the second CPU 14a (refer to step S19 in FIG. 3). Next, the correction image data are reconstructed (refer to step S20 to step S23 in FIG. 3).

Then, the correction image data and the original image data are added to each other. As a result, the image data performed the beam hardening correction is produced (refer to step S24 in FIG. 3). This image data are sent to the image data memory unit 17 and the image display unit 18 (refer to step S6 in FIG. 2). Consequently, the image data are displayed on the image display unit 18.

Figure 4:
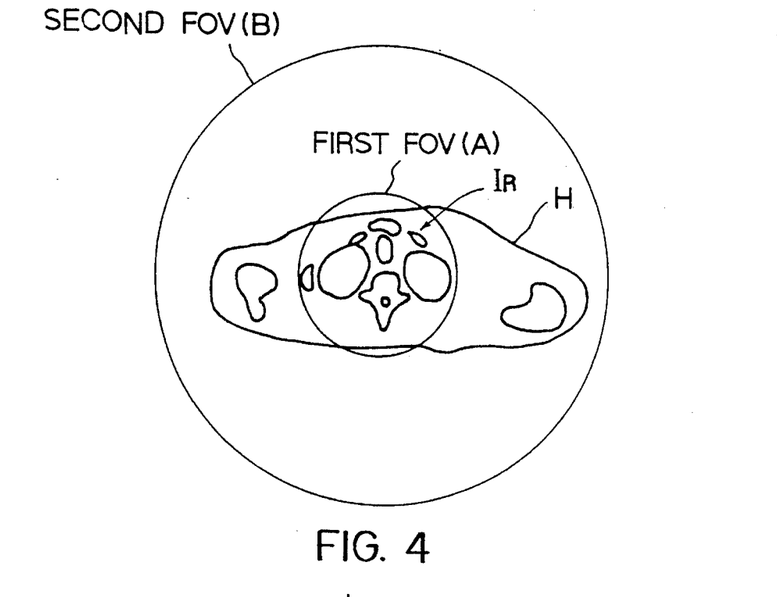
FIG. 4 is a diagram illustrating a first field of view and second field of view set on the imaged region.

On the other hand, at that time, if the operator wants to perform the magnification display of the interested area in the imaged region while the operator watches the image displayed on the image display unit 18, the operator, as shown in FIG. 4, sets the first FOV (A) whose area is smaller than the area of the imaged region according to operate the console panel. That is, the first FOV (A) includes the interest area $I_R$ but does not include the imaged region H wholly.

Then, the operator operates the console panel so as to output the scan performing order to the CPU 12a and the second CPU 14a.

At this time, the CPU 12a performs the foregoing process and the second CPU 14a performs the foregoing process at steps S1 to S4. Further, the CPU 14a performs the process on step S5, that is the second CPU 14a performs the process on step S10.

Namely, the second CPU 14a detects each CT-value of the plurality of pixels which are located in the circumference of the image data in order to judge whether or not the imaged region H is larger in area than the original image data corresponding to the first FOV (A) (refer to step 10 in FIG. 3). Now, as the first FOV (A) does not include the imaged region H wholly, all the detected CT-values is not the CT-value of the air as shown in FIG. 4. Therefore, it is judged that the imaged region is larger than the first FOV (A) (judge is YES) (refer to step S11 in FIG. 3).

According to the judgement on step S11, the second FOV (B) including the whole imaged region is set and the image data which are included in the second FOV (B) are reconstructed (refer to step S12 and S13 in FIG. 3).

Next, the plurality of the correction projection data are computed (refer to step S14 to step 16 in FIG. 3) and the correction image data are reconstructed on the basis of the first FOV (A) by using the correction projection data (refer to step S17 in FIG. 3). Then, the correction image data and the original image data are added to each other. As a result, the image data performed the beam hardening correction are produced (refer to step S18 in FIG. 3).

This image data are sent to the image data memory unit 17 and the image display unit 18 (refer to step S6 in FIG. 2). Consequently, the image data are displayed on the image display unit 18.

That is, it is possible to perform the BHC process easily by using the second FOV which includes the imaged region in case the first FOV is not larger than the imaged region in order to display the interest area in magnification state. Therefore, most of the artifacts which appear in the reconstructed image may be reduced.

Moreover, as the process of the second CPU 14a at steps S10 and S11 in FIG. 3, the operator may perform it by manual operation. That is, the operator recognizes that the imaged region is larger than the first FOV (A), watching the reconstructed image displayed on the image display unit 18. Next, the operator sets the second FOV (B) including the imaged region wholly by operating the console panel.

Still further, one of other methods for judgement in the process of the second CPU 14a at step S10 is as follows.

Figure 5:
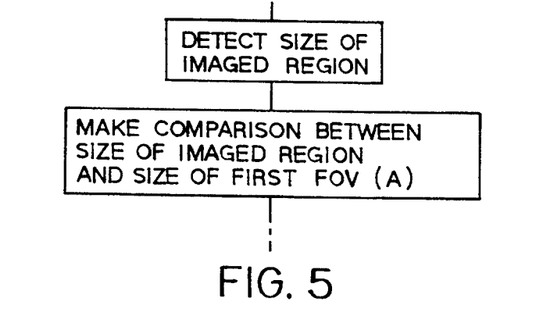
FIG. 5 is a segmentary schematic flow chart showing an other example of the process of the second central processing unit corresponding to step S10 in FIG. 2.

For example, as shown in FIG. 5, the second CPU 14a detects the size of the imaged region on the basis of the X-ray data detected with the channels of the X-ray detector 6. Namely, the second CPU 14a detects the position of the channels in which the X-ray data are stored (refer to step S10a in FIG. 5). Next, the second CPU 14a judges whether or not the imaged region is larger than the image data corresponding to the first FOV (A) by means of making comparison between the size of the imaged region and the size of the first FOV (A) (refer to step S10b in FIG. 5).

Furthermore, in case that the operator sets the zooming display according to operating the console panel with the input unit 13, the FOV set on zooming display is smaller in area than the imaged region clearly. Consequently, as judgement process of the second CPU 14a at steps S10 and S11 in FIG. 3, the second CPU 14a may detect whether or not the signals for performing the zooming display from the input unit 13 are inputted in the CPU 14a. As a result, in case that the signals are inputted in the CPU 14a, the CPU 14a may judge that the imaged region is larger than the FOV.

Figure 6:
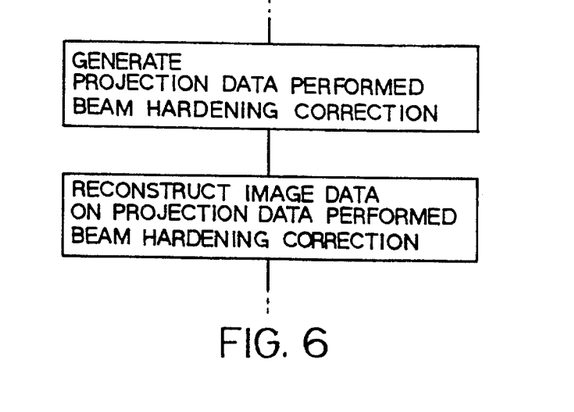
FIG. 6 is a segmentary schematic flow chart showing an other example of the process of the second central processing unit corresponding to steps S17 and S18 in FIG. 2.

In addition, the process of the second CPU 14a at steps S17 to S18 in FIG. 3 are not limited in this embodiment. For example, as shown in FIG. 6, the second CPU 14a, instead of step S17, synthesizes the plurality of projection data performed the preprocess and the correction projection data so as to produce a plurality of projection data performed beam hardening correction (refer to step S17a in FIG. 6). Next, the second CPU 14a, instead of step S18, reconstructs the image data on the basis of the projection data performed beam hardening correction according to the (first) FOV (refer to step S18a in FIG. 6). That is, the image data performed the beam hardening correction are produced.

Still further, in the process of the second CPU 14a at step S13 in FIG. 3, in case that the second CPU 14a uses the water phantom data with the second FOV, not the water phantom data used with the first FOV, the second CPU 14a need not add the CT-value of −1000 to the pixel out of the second FOV and may compute the X-ray path length directly.

While the invention has been particularly shown and described with reference to the preferred embodiment thereof, it will be understood by those skilled in the art that the foregoing and other changes in form and details can be made therein without departing from the spirit and scope of the invention.

What is claimed is:

1. An X-ray CT scanner, in which an image is produced on the basis of a plurality of projection data of an object being examined and the image is displayed, the scanner comprising:

means for setting a first field of view corresponding to a reconstructed area of the image;

means for reconstructing original image data on the basis of the projection data in response to the first field of view;

means for judging whether or not an imaged region in the object is larger than the first field of view;

means for setting a second field of view including the imaged region wholly in case that the imaged region is larger than the first field of view;

means for producing beam hardening correction data on the basis of the projection data in the second field of view; and means for processing the projection data into the image corresponding to the first field of view with an aid of the correction data.

2. The X-ray CT scanner according to claim 1, wherein said judgement is performed automatically.

3. The X-ray CT scanner according to claim 2, wherein said judgement means is comprised of an element for detecting each CT-value of a plurality of pixels located in a circumference of the original image data and an element for judging whether or not the each CT-value is CT-value of air.

4. The X-ray CT scanner according to claim 2, wherein said judgement means is comprised of an element for detecting a size of the imaged region on the basis of the projection data of the object and an element for comparing the size with a size of the first field of view.

5. The X-ray CT scanner according to claim 1, wherein said second field of view set means is comprised of setting the second field of view by manual operation.

6. The X-ray CT scanner according to claim 1, wherein said beam hardening correction data are composed of correction components of the projection data.

7. The X-ray CT scanner according to claim 6, wherein said projection data processing means comprises means for reconstructing correction image data composed of correction components of the original image data by using the correction data according to the first field of view and means for producing the image by synthesizing the correction image data and the original image data.

8. The X-ray CT scanner according to claim 6, wherein said projection data processing means comprises means for producing a plurality of projection data performed beam hardening correction by synthesizing the projection data and the correction data and means for reconstructing the image by using the projection data performed beam hardening correction on the basis of the first field of view.

9. A method of collecting image data in an X-ray CT scanner, in which an image is produced on the basis of a plurality of projection data of an object being examined and the image is displayed, the method comprising:

setting a first field of view corresponding to a reconstructed area of the image;

reconstructing original image data on the basis of the projection data in response to the first field of view;

judging whether or not an imaged region in the object is larger than the first field of view;

setting a second field of view including the imaged region wholly in case that the imaged region is larger than the first field of view;

producing beam hardening correction data on the basis of the projection data in the second field of view; and processing the projection data into the image corresponding to the first field of view with an aid of the correction data.

* * * * *

UNITED STATES PATENT AND TRADEMARK OFFICE
CERTIFICATE OF CORRECTION

PATENT NO. : 5,528,644
DATED : June 18, 1996
INVENTOR(S) : Yukihiro OGAWA, Yusuke TOKI It is certified that error appears in the above-indentified patent and that said Letters Patent is hereby corrected as shown below:

In column 2, line 6, after "appear" insert --on--.

In column 2, line 15, delete "is".

In column 5, line 9, after "data" insert --)--.

In column 7, line 65, change "performed" to --including--.

In column 8, line 40, change "performed" to --including--.

In column 9, line 19, change "performed" to --including--.

In column 9, line 20, change "performed" to --including--.

UNITED STATES PATENT AND TRADEMARK OFFICE
CERTIFICATE OF CORRECTION

PATENT NO. : 5,528,644
DATED : June 18, 1996
INVENTOR(S) : Yukihiro OGAWA, Yusuke TOKI It is certified that error appears in the above-indentified patent and that said Letters Patent is hereby corrected as shown below:

In column 9, line 23, change "performed" to --including--.

In column 9, line 26, change "performed" to --including--.

In column 10, line 5, change "judgment" to --judging--.

In column 10, line 7, delete "judgement"; same line, after "means" insert --for judging--.

In column 10, line 12, delete "judgement"; same line, after means, insert --for judging--.

In column 10, line 18, after "said" insert --means for setting--; same line, delete "set means".

UNITED STATES PATENT AND TRADEMARK OFFICE
CERTIFICATE OF CORRECTION

PATENT NO. : 5,528,644
DATED : June 18, 1996
INVENTOR(S) : Yukihiro OGAWA, Yusuke TOKI It is certified that error appears in the above-indentified patent and that said Letters Patent is hereby corrected as shown below:

In column 10, line 24, after "said" insert --means for processing--; same line, delete "processing means".

In column 10, line 31, after "said" insert --means for processing--; same line, delete "processing means".

Signed and Sealed this

Fifteenth Day of April, 1997

Attest:

BRUCE LEHMAN

*Attesting Officer*      *Commissioner of Patents and Trademarks*